United States Patent
Liu et al.

(10) Patent No.: US 8,715,607 B2
(45) Date of Patent: May 6, 2014

(54) METHOD FOR SEPARATING AND COLLECTING CARBON NANOTUBE, AND CARBON NANOTUBE

(75) Inventors: Huaping Liu, Ibaraki (JP); Takeshi Tanaka, Ibaraki (JP); Hiromichi Kataura, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 13/582,785

(22) PCT Filed: Mar. 3, 2011

(86) PCT No.: PCT/JP2011/054968
§ 371 (c)(1),
(2), (4) Date: Nov. 1, 2012

(87) PCT Pub. No.: WO2011/108666
PCT Pub. Date: Sep. 9, 2011

(65) Prior Publication Data
US 2013/0052120 A1  Feb. 28, 2013

(30) Foreign Application Priority Data
Mar. 5, 2010  (JP) .................. 2010-049766

(51) Int. Cl.
*G01N 30/02* (2006.01)
*D01F 9/12* (2006.01)
*B82Y 40/00* (2011.01)
*B82Y 30/00* (2011.01)

(52) U.S. Cl.
USPC .......... 423/447.2; 209/10; 977/845; 977/742; 210/635

(58) Field of Classification Search
None
See application file for complete search history.

(56) References Cited

U.S. PATENT DOCUMENTS

2003/0168385 A1* 9/2003 Papadimitrakopoulos ....... 209/1
2010/0230341 A1* 9/2010 Toumi ........................ 210/198.2
2010/0278714 A1 11/2010 Tanaka et al.

FOREIGN PATENT DOCUMENTS

JP        6-228824      8/1994
JP       2004-142972    5/2004

(Continued)

OTHER PUBLICATIONS

Chirality-Dependent Combustion of Single-Walled Carbon Nanotubes J. Phys. Chem. C (2007), V 111, pp. 9671-9677 Yasumitsu Miyata et al.*

(Continued)

*Primary Examiner* — Melvin C Mayes
*Assistant Examiner* — Douglas Call
(74) *Attorney, Agent, or Firm* — Wenderoth, Lind & Ponack, L.L.P.

(57) ABSTRACT

Metallic CNTs and semiconducting CNTs are efficiently separated from a CNT mixture of these CNTs, and semiconducting CNTs are separated by structure by using a method that enables separation in high yield in a short time period while conveniently enabling mass processing and automatic processing with inexpensive equipment.

Multiple columns charged with gel are connected in series, and excess amounts of a CNT dispersion is passed through the columns to adsorb only the CNTs of a specific structure on the columns. The CNTs are then eluted with an elution to separate CNTs of different structures with high accuracy. The present technique represents a method that conveniently enables mass processing and automatic processing at high yield in a short time period with inexpensive equipment.

7 Claims, 14 Drawing Sheets

(56) References Cited

FOREIGN PATENT DOCUMENTS

| | | |
|---|---|---|
| JP | 2005-104750 | 4/2005 |
| JP | 2005-194180 | 7/2005 |
| JP | 2005-325020 | 11/2005 |
| JP | 2006-282418 | 10/2006 |
| JP | 2007-031238 | 2/2007 |
| JP | 2008-285386 | 11/2008 |
| JP | 2008-285387 | 11/2008 |
| JP | 2011-195431 | 10/2011 |
| WO | 03/084869 | 10/2003 |
| WO | 2004/048256 | 6/2004 |
| WO | WO/2011/152788 * 8/2011 ............ 210/85 |

OTHER PUBLICATIONS

Continuous Separation of Metallic and Semiconducting Carbon Nanotubes Using Agarose Gel Applied Physics Express 2, (2009), 125002.1 to 125002.3 Takeshi Tanaka et al.*

International Search Report issued Apr. 26, 2011 in International (PCT) Application No. PCT/JP2011/054968, of which the present application is the national stage.

Kataura, "Separation and optical evaluation of single-wall carbon nanotubes", Nanotechnology Research Institute, National Institute of Advanced Industrial Science and Technology, vol. 78, No. 12, Dec. 10, 2009, pp. 1128-1134.

Tanaka et al., "Continuous, Repeatable Separation of Metallic and Semiconducting Carbon Nanotubes Using Agarose Gel", The Japan Society of Applied Physics and the Related Societies, Extended Abstracts of the 57$^{th}$ Spring Meeting, Mar. 3, 2010, p. 18p-TD-6.

Tanaka et al., "Continuous Separation of Metallic and Semiconducting Carbon Nanotubes Using Agarose Gel", Applied Physics Express, The Japan Society of Applied Physics, vol. 2, No. 12, pp. 125002.1-125002.3, 2009.

Tanaka et al., "Continuous Separation of Metallic and Semiconducting Carbon Nanotubes Using Agarose Gel", Abstracts: The 37$^{th}$ Fullerene-Nanotubes General Symposium, The Fullerenes and Nanotubes Research Society, Nanotechnology Research Institute, National Institute of Advanced Industrial Science and Technology (AIST), Sep. 1, 2009, p. 22.

Ralph Krupke et al., "Thin Films of Metallic Cabon Nanotubes Prepared by Dielectrophoresis", Advanced Materials, 2006, vol. 18, pp. 1468-1470.

Yutaka Maeda et al., "Large-Scale Separation of Metallic and Semiconducting Single-Walled Carbon Nanotubes", J. Am. Chem. Soc., 2005, vol. 127, pp. 10287-10290, with supporting information.

Yutaka Maeda et al., "Dispersion and Separation of Small-Diameter Single-Walled Carbon Nanotubes", J. Am. Chem Soc., 2006, vol. 128, pp. 12239-12242, with supporting information.

Yasumitsu Miyata et al., "Selective Oxidation of Semiconducting Single-Wall Carbon Nanotubes by Hydrogen Peroxide", The Journal of Physical Chemistry B, 2006, vol. 110, pp. 25-29.

Michael S. Arnold et al., "Sorting carbon nanotubes by electronic structure using density differentiation", Nature Nanotechnology, Oct. 2006, vol. 1, pp. 60-65, with supporting information.

Takeshi Tanaka et al., "Simple and Scalable Gel-Based Separation of Metallic and Semiconducting Carbon Nanotubes", Nano Letters, 2009, vol. 9, No. 4, pp. 1497-1500, with supporting information.

Xiaomin Tu et al., "DNA sequence motifs for structure-specific recognition and separation of carbon nanotubes", Nature, Jul. 9, 2009, vol. 460, pp. 250-253.

* cited by examiner

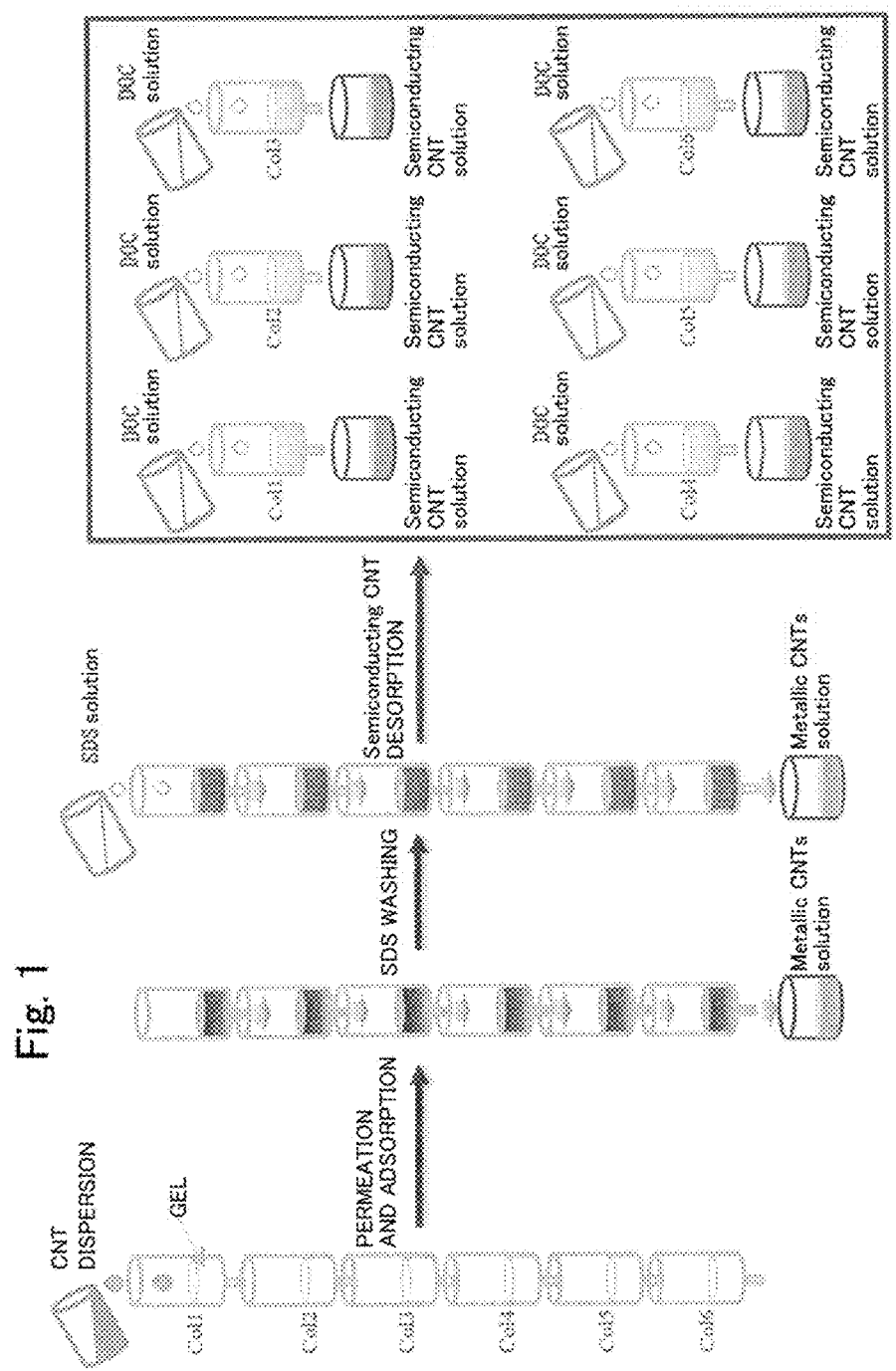

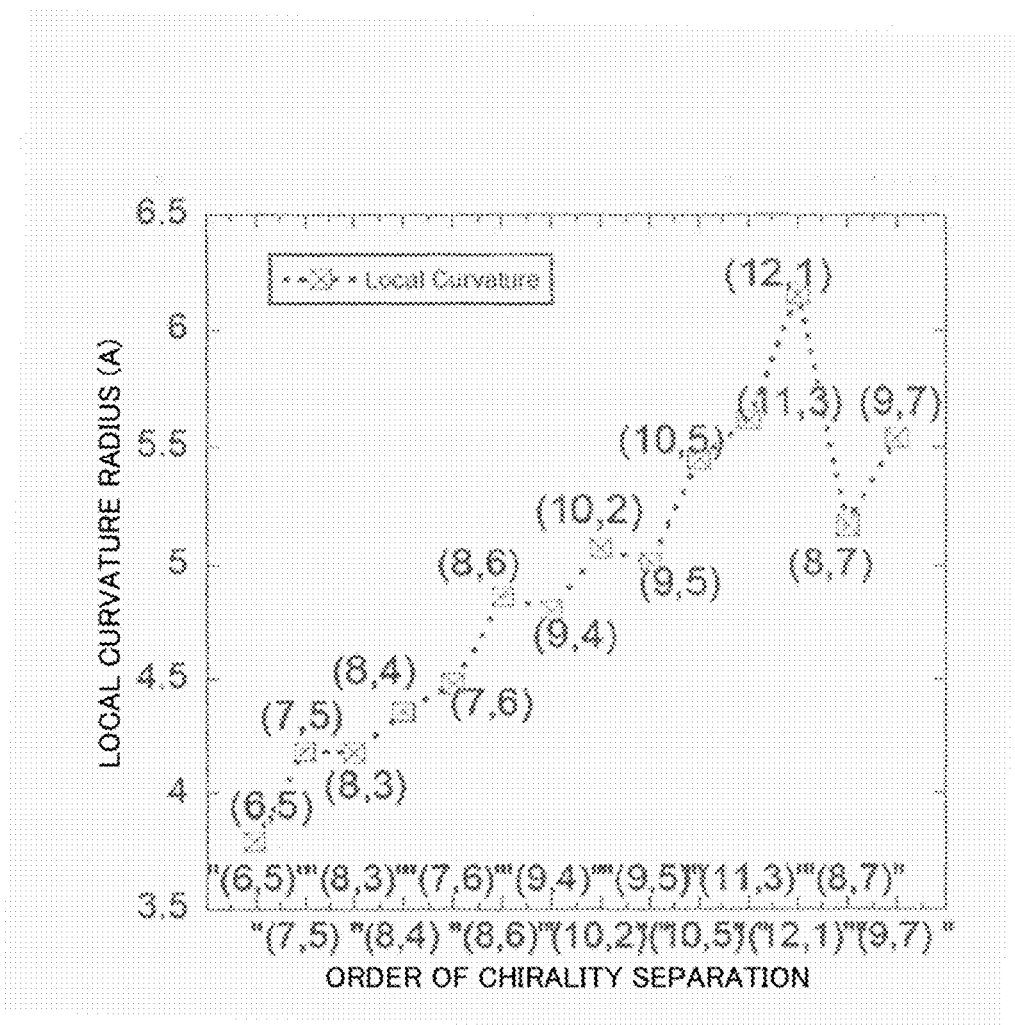

METHOD FOR SEPARATING AND COLLECTING CARBON NANOTUBE, AND CARBON NANOTUBE

TECHNICAL FIELD

The present invention relates to a method for efficiently separating metallic carbon nanotubes and semiconducting carbon nanotubes from carbon nanotubes (CNTs) containing these carbon nanotubes, and for separating the semiconducting CNTs by structure. The present invention also relates to carbon nanotubes obtained by using the method.

BACKGROUND ART

CNTs have excellent electrical characteristics and mechanical strength along with other superior properties, and have been actively researched and developed as an ultimate novel material. CNTs are synthesized by using various methods, including a laser vaporization method, an arc discharge method, and a chemical vapor deposition method (CVD method). However, CNTs produced by using any of the currently available synthesis methods are obtained as a mixture of metallic CNTs and semiconducting CNTs.

Because either one of the metallic and semiconducting properties is often used in actual use, separation and purification of only the metallic or semiconducting CNTs from a CNT mixture is an urgent and important research subject. Further, because different structures (including diameter and chirality; described later) of semiconducting CNTs provide different properties, a technique for obtaining semiconducting CNTs of a uniform structure is strongly needed.

There are reports of separating metallic CNTs and semiconducting CNTs. However, all of these reports pose problems in industrial production of metallic CNTs and semiconducting CNTs, as follows. (1) The separation involves complicated steps, and cannot be automated; (2) the separation is time consuming; (3) mass processing is not possible; (4) expensive equipment and chemicals are required; (5) only one of the metallic CNTs and semiconducting CNTs are obtained; and (6) the collection rate is low.

Examples of the currently available methods include a method in which CNTs dispersed with a surfactant are subjected to dielectrophoresis on microelectrodes (Non-Patent Document 1), a method in which amines are used as the dispersant in a solvent (Non-Patent Documents 2 and 3), and a method for selectively burning semiconducting CNTs with hydrogen peroxide (Non-Patent Document 4). However, these techniques also have the foregoing problems. Particularly, the final material is limited to metallic CNTs, and the collection rate is low.

Other methods includes a method in which a mixture of semiconducting CNTs and metallic CNTs is dispersed in a liquid to selectively bind the metallic CNTs to particles, and in which the metallic CNTs attached to the particles are removed to separate the semiconducting CNTs (Patent Document 1), a method in which CNTs treated with a nitronium ion-containing solution are filtered and heat treated to remove the metallic CNTs contained in the CNTs and to obtain semiconducting CNTs (Patent Document 2), a method using sulfuric acid and nitric acid (Patent Document 3), and a method in which CNTs are selectively separated by migration under applied electric field to obtain semiconducting CNTs confined within a narrow electric conductivity range (Patent Document 4).

These techniques also have the foregoing problems. Particularly, the resulting final material is limited to semiconducting CNTs, and the collection rate is low.

There is also a method in which CNTs dispersed with a surfactant are separated into metallic CNTs and semiconducting CNTs by density-gradient ultracentrifugal separation (Non-Patent Document 5). This technique is also problematic, because the method uses a very expensive ultracentrifugal separator, and requires a long time for the ultracentrifugal separation procedure. Further, because the ultracentrifugal separator can only be increased to a certain size, more than one ultracentrifugal separator needs to be installed in parallel, and accordingly automation and other processes are difficult.

In another method, separation is achieved by ion-exchange chromatography using a CNT-nucleic acid complex of CNTs attached to nucleic acid molecules (Patent Document 5). A problem of this method, however, is that it requires an expensive synthetic DNA, and that the collection rate and purity are poor because of the moderate separation accuracy.

Further, there is a report directed to separating metallic CNTs and semiconducting CNTs under electric field after causing protonation in different extents for different CNTs by adjusting the pH or ion strength of a CNT solution prepared by dispersing the CNTs with a surfactant (Patent Document 6). However, in this method, a pretreatment step needs to be performed before separation with the use of a strong acid for the pH and ion-strength adjustments of a suspended nanotube mixture. The method thus inevitably involves strict step control, and does not successfully separate metallic CNTs and semiconducting CNTs (Patent Document 6, Example 4).

Separation of semiconducting CNTs by diameter or structure also involves problems similar to those identified in the separation of metallic CNTs and semiconducting CNTs.

CNTs can be separated by diameter by density-gradient ultracentrifugal separation (Non-Patent Document 5). However, the technique has problems as above, including the need to use a very expensive device, a long separation time, limited size, and difficulties in implementing automation and other processes.

There is also a report of separating a CNT structure by ion-exchange chromatography using a CNT-nucleic acid complex (Patent Document 7). However, the method is problematic, because it requires a specific synthetic DNA for the CNTs of each individual structure, and that the synthetic DNA is very expensive.

As described above, all of the conventional methods are insufficient for overcoming the foregoing problems, and there is a need for developing a method based on new ideas whereby metallic CNTs and semiconducting CNTs can be separated from CNTs, and whereby semiconducting CNTs of a specific structure can be separated.

The present inventors have worked on a novel method that differs from any of the conventional methods for separating metallic CNTs and semiconducting CNTs, and completed the inventions below (Patent Documents 9, 10, 11, and 12). These inventions enable separation of semiconducting CNTs from metallic CNTs by the selective adsorption of the semiconducting CNTs by a gel used in combination with specific types of dispersant. The semiconducting CNTs adsorbed to the gel are separated from the unadsorbed CNTs by methods such as electrophoresis (Patent Documents 9 and 10), and centrifugation or freeze squeeze, diffusion, and permeation (Patent Document 11). These methods are highly desirable, because both the metallic CNTs and the semiconducting CNTs are obtained, and because the methods enable separation in a short time period at high collection rate, and conveniently enable mass processing with inexpensive equipment.

The present inventors also completed a method that uses a suitable elution for the collection of semiconducting CNTs adsorbed on a gel (Patent Document 12). Specifically, a CNT dispersion is passed through a gel to allow semiconducting CNTs to be adsorbed by the gel. The unadsorbed metallic CNTs are then eluted and separated from the gel, and the semiconducting CNTs adsorbed on the gel are collected with an elution. This technique is very desirable, because the method enables the gel to be used repeatedly, and the separation to be automated for the industrial mass production of metallic and semiconducting CNTs.

In a similar technique invented by the present inventors, the elution concentration is adjusted, and CNTs are separated by diameter simultaneously with the separation of metallic CNTs and semiconducting CNTs (Patent Document 12). This technique is very desirable, because CNTs having different diameters can be obtained simultaneously with the separation of metallic CNTs and semiconducting CNTs, and because the method conveniently enables mass processing and automatic processing in a short time period at high yield with inexpensive equipment.

However, the method suffers from low accuracy in the diameter-specific separation, and requires further improvement for obtaining semiconducting CNTs having a uniform structure.

Patent Document 1: JP-A-2007-31238
Patent Document 2: JP-A-2005-325020
Patent Document 3: JP-A-2005-194180
Patent Document 4: JP-A-2005-104750
Patent Document 5: JP-A-2006-512276
Patent Document 6: JP-A-2005-527455
Patent Document 7: JP-A-2004-142972
Patent Document 8: JP-A-2006-282418
Patent Document 9: JP-A-2008-285386
Patent Document 10: JP-A-2008-285387
Patent Document 11: WO2009/075293
Patent Document 12: Japanese Patent Application No. 2009-147557
Non-Patent Document 1: Advanced Materials 18, (2006) 1468-1470
Non-Patent Document 2: J. Am. Chem. Soc. 127, (2005) 10287-10290
Non-Patent Document 3: J. Am. Chem. Soc. 128, (2006) 12239-12242
Non-Patent Document 4: J. Phys. Chem. B 110, (2006) 25-29
Non-Patent Document 5: Nature Nanotechnology 1, (2006) 60-65
Non-Patent Document 6: Nano Letters 9, (2009) 1497-1500
Non-Patent Document 7: NATURE 460, (2009) 250-253

DISCLOSURE OF INVENTION

Problems to be Solved by the Invention

The present invention has been made under these circumstances, and it is an object of the present invention to provide a method for separating metallic CNTs and semiconducting CNTs, and for accurately separating semiconducting CNTs of different structures. The present invention also provides carbon nanotubes obtained by using the method.

Means for Solving the Problems

The present inventors conducted studies to solve the foregoing problems, and found that semiconducting CNTs of a single structure can be separated by causing a large excess of CNT dispersion to act on small amounts of gel. Further, semiconducting CNTs of different structures can be separated and collected at once by causing the semiconducting CNTs to be adsorbed on a plurality of columns charged with a gel and connected in series by addition of a large excess of a CNT dispersion to the columns (FIG. 1).

Generally, improving the accuracy of the separation that uses columns is tackled by adding a sample in amounts below the binding capacity of a support, or by reducing the amount of sample used. The present invention takes the completely opposite approach, and improves separation accuracy by intentionally adding a sample in large excess. The present invention can thus be said as a unique novel separation method. It is believed that the high-accuracy separation is achieved among the existing wide variety of substances by first binding a material having high affinity to the support only, and then separating the material from the remaining materials.

The present invention has been completed based on these novel findings.

Specifically, this application provides the following invention.

<1> A method for separating and collecting a carbon nanotube, the method including causing a carbon nanotube dispersion to act in excess amount on a gel charged in a column to make the gel adsorb a carbon nanotube having strong gel adsorbability and to separate a solution containing an unadsorbed carbon nanotube having weak gel adsorbability from the gel adsorbing the carbon nanotube; and causing an elution to act on the gel after the separation to remove the carbon nanotube adsorbed by the gel.

<2> A method for separating and collecting a carbon nanotube, the method including causing a carbon nanotube dispersion to act in excess amount on a gel charged in a column in the first of n stages of columns connected in series (n≥2, where n is a natural number) and causing the carbon nanotube dispersion to act on the column of the first stage until the carbon nanotube adsorbs to a gel in the column of the nth stage to separate a carbon nanotube having the first to the nth strongest adsorbability and adsorbed to the gel in each column in the n stages of columns from a solution containing a weakly adsorbable carbon nanotube adsorbed by neither of the gels in the columns; and causing an elution to individually act on the columns to remove the n kinds of carbon nanotubes having different levels of adsorbability and adsorbed to the gels in the respective columns.

<3> The method according to <1> or <2>, wherein the carbon nanotube dispersion used in excess amount for the gel is a dispersion that contains the carbon nanotube in excess of the carbon nanotube amount adsorbable by the column.

<4> The method according to <1> or <2>, wherein a strongly adsorbable semiconducting carbon nanotube of a specific structure is removed from the gel after the separation.

<5> The method according to <4>, wherein a semiconducting carbon nanotube having a specific diameter as the specific structure is removed from the gel after the separation.

<6> The method according to <4>, wherein a semiconducting carbon nanotube having specific chirality as the specific structure is removed from the gel after the separation.

<7> The method according to <4>, wherein a semiconducting carbon nanotube having a specific local curvature radius as the specific structure is removed from the gel after the separation.

<8> The method according to <2>, wherein the carbon nanotube dispersion that acts on the gel charged in the column of the nth stage has a lower concentration than the carbon nanotube dispersion that acts on the gel charged in the column of the (n−1)th stage.

<9> A carbon nanotube that has strong adsorbability to a gel and is obtained by causing a carbon nanotube dispersion to act on the gel charged in the column of <1> or <2> in excess amount for the gel.

<10> A carbon nanotube that is unadsorbable by a gel obtained by the method of <1> or <2>.

Advantage of the Invention

The present invention enables semiconducting CNTs to be separated by structure simultaneously with the separation of metallic CNTs and semiconducting CNTs. The invention also enables semiconducting CNTs of a specific structure to be separated from a mixture of semiconducting CNTs. The invention is applicable not only to continuous separation using a column, but to batch separation. More than one kind of semiconducting CNTs of specific structures can be obtained at once with high accuracy. In the foregoing technique for separating semiconducting CNTs of a single structure with the use of an expensive synthetic DNA (Non-Patent Document 7), a synthetic DNA of a specific sequence needs to be prepared for the CNTs of each different structure. In contrast, in the present invention, the same reagent may be used for the separation of semiconducting CNTs of each different structure, and the invention is very desirable in terms of ease of operation, and cost. Further, accurate separation is possible with inexpensive equipment, and the columns can be reused. It is also possible to automate the separation. These advantages can greatly reduce separation cost. Further, the method can be said as a very practical method, because it can separate semiconducting CNTs by structure, simultaneously with the separation of metallic CNTs and semiconducting CNTs.

BRIEF DESCRIPTION OF THE DRAWINGS

FIG. 1 is an explanatory diagram representing a method for separating and collecting semiconducting CNTs of a single structure with columns connected in series. A large excess of a CNT dispersion is added to a plurality of columns charged with a gel and connected in series to adsorb semiconducting CNTs of different structures to the columns. The columns are separated from one another after thoroughly washing out the CNT solution containing large amounts of unadsorbed metallic CNTs (the box on the right-hand side of the diagram), and the CNTs adsorbed to the columns are collected with an elution.

FIG. 8C represents the chirality order of the CNTs separated with series columns plotted against local curvature radius.

MODE FOR CARRYING OUT THE INVENTION

Figure 2A:
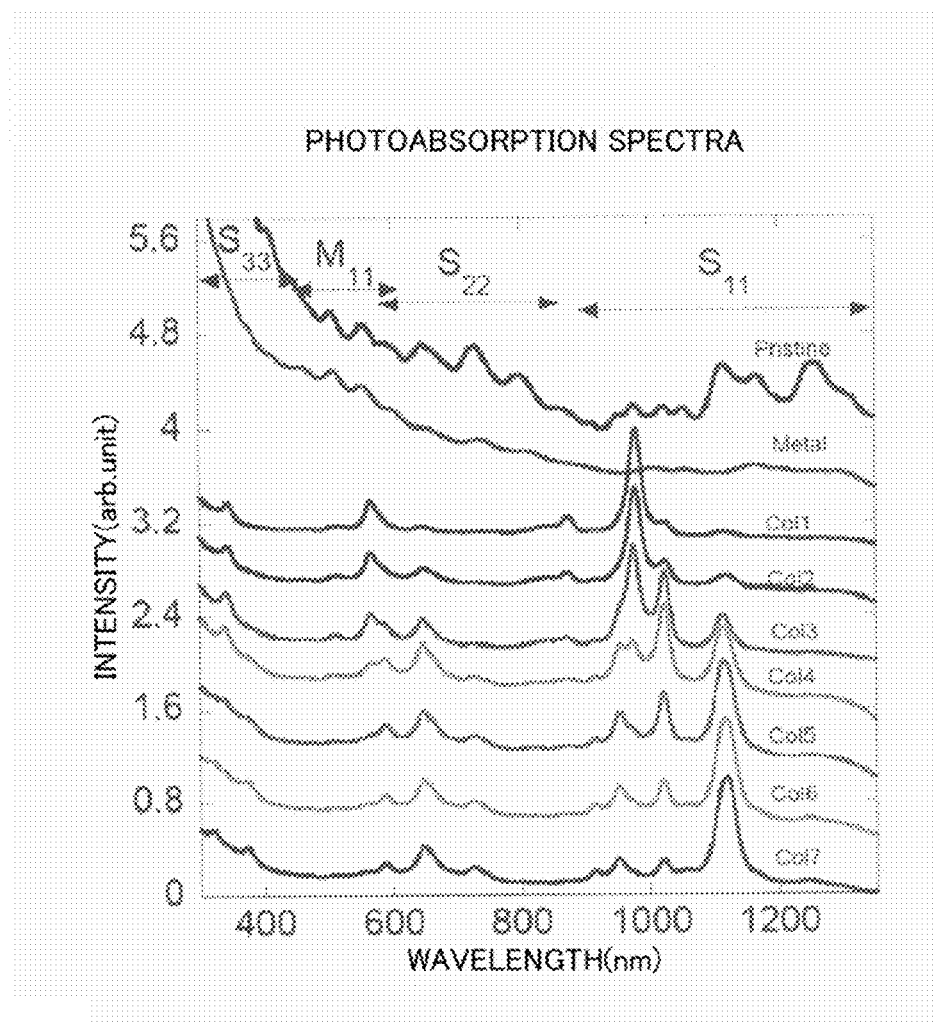
FIG. 2A represents photoabsorption spectra of a separated sample (HiPco-CNT).

The present invention is described below in detail.

As used herein, the carbon nanotubes of a "specific structure" separated and collected include those having clearly identifiable characteristics based on the specific structure defined by diameter, chirality, local curvature radius, and a combination of these, as compared with the characteristics before the separation procedure as measured by techniques such as ultraviolet-visible-nearinfrared absorption spectral measurement, fluorescence spectral measurement, and Raman spectral measurement. Accordingly, the carbon nanotubes of a specific structure after the separation and collection may be those having substantially a single structure, or a mixture of two or more specific structures extracted from the carbon nanotubes. Further, the carbon nanotubes of a specific structure may be a mixture containing slight amounts of carbon nanotubes having any other structure, provided that the selective separation and collection of the carbon nanotubes of a specific structure can be identified by measurements such as above.

The present invention is directed to a method for separating metallic CNTs and semiconducting CNTs, and for separating semiconducting CNTs of different structures, and to a method for separating CNTs of different structures from a mixture containing metallic CNTs and semiconducting CNTs (hereinafter, also referred to simply as "CNTs"), or from a mixture of semiconducting CNTs of different structures.

In the method for separating CNTs of different structures according to the present invention, only the CNTs having strong adsorbability are separated and purified by adding excess amounts of a CNT dispersion obtained as below to a gel charged in columns.

As used herein, the excess amounts of a CNT dispersion are amounts in excess of the carbon nanotube amounts that can be adsorbed by the gel charged in a column. Specifically, the excess amounts of a CNT dispersion are amounts by which the CNTs that can inherently adsorb to the gel are eluted without being adsorbed on a column upon being introduced into the column in increasing amounts as with the case of the CNTs that do not have the inherent property to adsorb to the column. In other words, the initial CNT amounts introduced into a column are excess amounts when the CNTs introduced into the column and collected without being adsorbed by the gel charged in the column still contain CNTs that can adsorb to the gel upon being reintroduced into a new column charged with the gel.

It is believed that the binding of only the CNTs of a specific structure occurs under the following principles when the excess amounts of a CNT dispersion act on the gel charged in the column. In response to the excess amounts of the CNT dispersion introduced into the column for the gel charged therein, adsorption by the gel takes place more preferentially for the CNTs of a specific structure having stronger adsorbability to the gel than for the CNTs having weaker adsorbability, and the CNTs having weaker adsorbability discharge without being adsorbed by the gel. As a result, only the CNTs having stronger adsorbability adsorb to the gel, and only the specific type of CNTs can be obtained.

More than one type of CNTs having different structures can be separated at once by adding excess amounts of a CNT solution to the gel charged in columns connected in series in multiple stages. Specifically, the CNTs of a structure having the strongest adsorbability adsorb to the first column, and the CNTs of a structure having the strongest adsorbability in the remaining CNTs that did not adsorb to the first column adsorb to the second column. In a similar fashion, the CNTs bind to the third, fourth, fifth, and the subsequent columns in order of decreasing adsorbability. As a result, CNTs having specific structures can be simultaneously separated.

The CNTs separated are not limited by the methods of production, the shape (including diameter and length), and the structure (for example, may be a double wall or single wall). Any CNTs can be the target of the separation by the present invention.

Generally, a CNT structure is primarily defined by the chiral indices represented by a set of two integers (n, m). The metallic CNTs and semiconducting CNTs as used in the present invention are distinguished by their electrical properties among the carbon nanotubes. The metallic CNTs are defined as having a chiral index n−m=(multiples of three), and the semiconducting CNTs as having a chiral index other than n−m=multiples of three (Non-Patent Document 8: Riichiro Saito, Hisanori Shinohara, *Basics and Applications of Carbon Nanotubes*, Baifukan, pp. 13 to 22).

Preparation of CNT Dispersion

Synthesized CNTs typically exist as bundles of several ten to several hundred metallic CNTs and semiconducting CNTs. For the separation of the metallic CNTs and the semiconducting CNTs, or for the separation of the CNTs by structure, it is important that the CNTs be stabilized for extended time periods by being dispersed and solubilized in the form of individual, isolated CNTs.

To this end, the CNT mixture is added to a solution containing a surfactant added as a dispersant, and the CNTs are dispersed and isolated by sufficient sonication. The liquid after the dispersion process contains the dispersed and isolated CNTs, CNT bundles that could not be dispersed and isolated, amorphous carbon as a synthesis by-product, a metal catalyst and the like.

The dispersion after the sonication is centrifuged with a centrifuge. The centrifugation settles the CNT bundles, the amorphous carbon, and the metal catalyst, whereas the isolated CNTs forming micelles with the surfactant can be collected with the supernatant. The supernatant can then be used as a sample for CNT separation.

Water is most preferred as the solvent used to prepare the CNT dispersion. Water is thus used to prepare the CNT dispersion.

Any of anionic surfactants, cationic surfactants, ampholytic surfactants, and non-ionic surfactants may be used as the surfactant.

Preferred examples of the anionic surfactants include alkylsulfuric acid surfactants of 10 to 14 carbon atoms, dodecanesulfonic acid, dodecanoylsarcosine, dodecanoic acid, and cholic acid. Preferred examples of the ampholytic surfactants include n-dodecylphosphocholine. These surfactants may be used as a mixture, or with other surfactants.

Aside from the anionic surfactants, the cationic surfactants, the ampholytic surfactants, and the non-ionic surfactants, the surfactants used with the foregoing surfactants may be dispersants such as polymer, DNA, and protein. The concentration of the surfactant and other dispersants may be, for example, 0.01% to 25% (final concentration), though the concentration depends on such factors as the type and concentration of the CNTs used, and the type of the dispersant used.

In this way, the CNT concentration in the dispersion can be brought to 1 µg/ml to 10 mg/ml, preferably 0.1 mg/ml to 1 mg/ml. For example, the amount of the sample added may be greater than the binding capacity of the gel support by several factors to several ten factors, through the amount varies according to the number of materials to be separated in the sample, and the composition ratio.

Gel

The gel used may be common carbohydrate gels, including dextran gels (Sephacryl: a cross-linked copolymer of allyldextran and N,N'-methylenebisacrylamide; GE healthcare), agarose gel, and starch gel. Acrylamide gel may also be used. It is also possible to use mixtures of these gels, or gels containing the constituent components of these gels, and mixtures and compounds of other materials.

The gel concentration may be, for example, 0.01% to 25% (final concentration).

The separation by the present invention is not limited to the method using a column, and, for example, a batch method may be used in which a small amount of gel is added to a large excess of a CNT dispersion to cause only the material having strong adsorbability to adsorb to the gel for the separation and collection.

In the separation using a column, the liquid may be sent into the column by using various methods, including a method that takes advantage of the free fall of the solvent in an open column, and a method that sends the solution into a closed column with a pump. In the separation using a pump, the flow rate may be increased to perform mass processing. Automated separation is also possible with the use of a chromatographic apparatus. The whole separation process may be automated even with the columns connected in series, provided that suitable valves are disposed in front of and behind the columns.

CNTs that have weak bondability and cannot easily adsorb to the gel can be separated by increasing adsorbability. This can be achieved by, for example, varying the concentration of the dispersant in the solution used for the separation.

Dispersants such as surfactants may be used to collect the CNTs adsorbed to the gel.

Ultraviolet-visible-nearinfrared absorption spectral measurement is used to estimate the proportions of the metallic CNTs and semiconducting CNTs.

As an example, this is described by using the result from CNTs obtained by HiPco synthesis (HiPco-CNTs, diameter 1.0±0.3 nm) (FIG. 2A, Pristine). The absorption wavelength band (about 450 to 650 nm) called $M_{11}$ is of the metallic CNTs. The three absorption wavelength bands $S_{11}$ (about 900 nm and higher), $S_{22}$ (about 650 to 900 nm), and $S_{33}$ (about 450 nm and lower) result from the semiconducting CNTs. Here, the proportions of the metallic CNTs and the semiconducting CNTs are estimated from the proportions of the $M_{11}$ and $S_{22}$ peak sizes. The absorption wavelength bands ($M_{11}$, $S_{11}$, $S_{22}$, $S_{33}$) vary according to the average diameter of the measured CNTs. The absorption wavelength bands shift toward the shorter wavelength side with decreasing average diameters, and toward the longer wavelength side with increasing average diameters.

CNT absorption overlaps in the photoabsorption spectral measurement, and one cannot tell whether a single peak is due to single CNTs, or due to an overlap of the peaks of more than one type of CNTs. In order to distinguish and detect individual metallic CNTs and semiconducting CNTs, Raman spectroscopy measurement was used. FIG. 2C (Pristine) represents the result of the measurement of an unseparated HiPco-CNT sample excited with a 633-nm laser beam. Peaks with the wavenumbers 254, 265, 284, and 298 $cm^{-1}$ derive from the semiconducting CNTs, and the 197 and 218 $cm^{-1}$ peaks from the metallic CNTs. The all peaks derive from CNTs of a single structure, and peaks with greater wavenumbers derive from CNTs of smaller diameters.

Figure 4A:
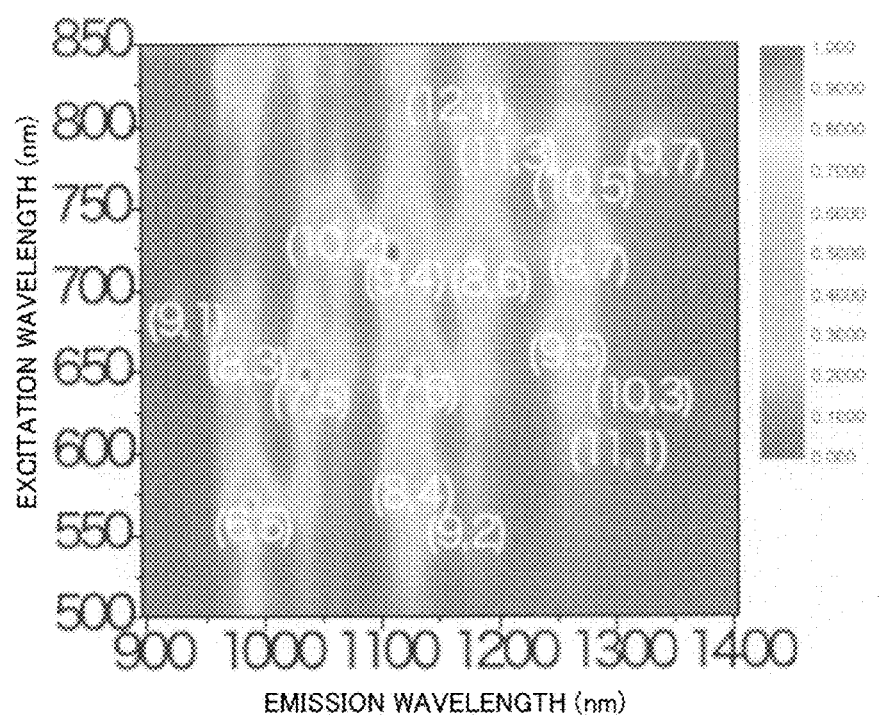
FIG. 4A represents the result of fluorescence spectral measurement (HiPco-CNT; before separation). The fluorescence intensity is represented by a contour plot of fluorescence wavelength (horizontal axis) against excitation wavelength (vertical axis). The figure indicates that the intensity increases in color density order of brighter spots to darker spots over the dark background (see the scale on the right of the figure). Main spots are appended with chiral indices.

The Raman spectroscopy measurement enables chirality-specific detection of the metallic CNTs and the semiconducting CNTs; however, only the information derived from some of the CNTs can be obtained. The fluorescence spectral measurement cannot be used for the measurement of metallic CNTs, but can distinguish and detect the semiconducting CNTs by chirality. FIG. 4A represents the result of the measurement of an unseparated HiPco-CNT sample. The result is represented as a contour plot that shows the fluorescence intensity in different color densities. The vertical axis and horizontal axis represent excitation wavelength and fluorescence wavelength, respectively. The fluorescence derived from the semiconducting CNTs of single chirality appears as spots. The corresponding chirality is indicated next to each spot.

EXAMPLES

The present invention is described below in more detail using examples. It should be noted that the present invention is not limited by the following examples.

Example 1

A CNT sample was added in large excess to a column to separate and collect semiconducting CNTs of single chirality.
Preparation of CNT Dispersion A 2% SDS aqueous solution (100 ml) was added to 100 mg of Hipco-CNTs (CNI; CNTs synthesized by chemical vapor deposition; diameter 1.0±0.3 nm). The solution was sonicated at a 20 $W/cm^2$ output for 20 hours while being cooled in cold water, using a tip-type ultrasonic homogenizer (Sonifier; Branson; tip diameter 0.5 inches). The dispersion resulting from the sonication was subjected to ultracentrifugal separation (197,000×g, 15 min) to collect 80% of the supernatant. The solution was then used as a CNT dispersion.
Column Preparation and Separation Gel beads (Sephacryl S-300; GE healthcare) were used as a column support. The gel beads were charged into a plastic column (length 7.5 cm; inner diameter 1.5 cm) until the height reached about 2 mm, and equilibrated with a 2% SDS aqueous solution after passing deionized water. A CNT dispersion (5 ml) was then added. Then, a 2% SDS aqueous solution was added to wash the column until the solution turned colorless transparent. The gel had a purple color after the washing. A 0.05% DOC aqueous solution (elution) was then added to collect the CNTs adsorbed on the column. The photoabsorption spectrum (FIG. 2A, Col1) and the fluorescence spectrum (FIG. 4B, Col1) of the resulting aqueous solution are represented.

Photoabsorption Spectral Measurement and Fluorescence Spectral Measurement

In a CNT photoabsorption spectrum of a single structure, absorption peaks $S_{11}$, $S_{22}$, and $S_{33}$ are observed from the longer wavelength side in semiconducting CNTs, and a peak $M_{11}$ is observed between $S_{22}$ and $S_{33}$ in metallic CNTs. These absorption peaks have different peak wavelengths for different diameters, and shift toward the longer wavelength side in CNTs having larger diameters, and toward the shorter wavelength side in CNTs having smaller diameters. The synthesized CNTs are a mixture of various types of CNTs of various diameters, and the photoabsorption spectrum is observed as an overlap of these mixture peaks. It can be seen from the results of photoabsorption spectral measurements represented in FIG. 2A, many peaks are recognized in the unseparated CNTs (Pristine), whereas only one peak is recognized in each of the $S_{11}$, $S_{22}$, and $S_{33}$ regions in CNTs that were adsorbed and eluted in the column (Col1), suggesting that semiconducting CNTs of single chirality were separated.

The photoabsorption spectrum may include an overlap of absorption peaks from other CNTs, and the peaks may not be distinguished. Fluorescence spectral measurement was thus performed that can distinguish and detect the individual chirality of the semiconducting CNTs. The measurement result is represented by a contour plot that shows the fluorescence intensity in different color densities. The vertical axis and horizontal axis represent excitation wavelength and fluorescence wavelength, respectively. The fluorescence derived from single semiconducting CNTs appears as spots. In contrast to the large numbers of spots recognized in the sample before separation (FIG. 4A), essentially only a single spot due to (6,5) CNTs was recognized in the spectrum of the separated sample.

These results show that CNTs of single chirality can be separated and collected by addition of a CNT dispersion in large excess to small amounts of a gel support.

Example 2

The same experiment conducted in Example 1 was performed by using a plurality of columns connected in series. CNTs of different chiralities were adsorbed in different columns at once, and, after separating the columns, the CNTs adsorbed in each column were collected to separate and collect the CNTs of different chiralities at once.
Column Preparation and Separation As represented in FIG. 1, six columns were connected in series. Sephacryl S-300 that provides desirable purity for the (6,5) CNTs was used for the columns of the first and second stages, though separation is possible with either of Sephacryl S-200 and Sephacryl S-300. Sephacryl S-300 was charged to the height of about 2 mm in the first column, and to the height of about 3.5 mm in the second column. Sephacryl S-200 was used for the third to sixth columns by being charged to the height of about 6 mm. Prior to the separation, the columns were equilibrated with deionized water and a 2% SDS aqueous solution in this order.

In the first round, a 5-ml CNT dispersion was added, and a 2% SDS aqueous solution was sent into the columns to remove the CNTs that do not adsorb to the columns. The columns were then separated from each other, and the CNTs adsorbed on each column were collected by being eluted with a 0.05% DOC aqueous solution (FIG. 1, the right box). The fractions eluted and collected from the first to sixth columns were named Col1 to Col6. The columns were washed with a 2% DOC aqueous solution, and reequilibrated with a 2% SDS aqueous solution for the next separation. In the second and subsequent separation runs, Sephacryl S-200 (height 6 mm) was used for all of the connected six columns. The CNT solution that did not adsorb on the columns and directly ran though the columns in the first separation was directly used as a sample. The fractions separated and collected were named Col7 to Col12.

In the next round, the concentration of the dispersant was lowered to enable the gel adsorption and the separation of the CNT dispersion that did not adsorb on the columns and directly ran though the columns in the second separation. Specifically, the CNT dispersion that directly ran through the columns was subjected to ultracentrifugal separation (197,000×g, 3 hours) to settle and concentrate. The solution was diluted to make the final concentration 1.5% SDS, and the volume was adjusted to 5 ml to obtain a separation sample. The separation was performed in the same manner as in the second separation, except that a 1.5% SDS aqueous solution was used to equilibrate the columns and to elute the unadsorbed CNTs. The resulting column adsorption fractions were named Col13 to Col18. The CNT solution that did not adsorb on the columns in the third separation was reintroduced into the columns, and separated with 1.5% SDS. The resulting fractions were named Col19 to Col24.

In the third round, the CNT solution that did not adsorb to the columns and directly ran through the columns in the fourth separation was subjected to ultracentrifugal separation (197,000×g, 3 hours) to concentrate. The solution was diluted to make the final concentration 1% SDS, and the volume was adjusted to 5 ml to obtain a separation sample. The separation was performed in the same manner as in the second separation, except that a 0.5% SDS aqueous solution was used to equilibrate the columns and to elute the unadsorbed CNTs. The resulting column adsorption fractions were named Col25 to Col30. The CNT solution that did not adsorb on the columns in the fifth separation was reintroduced into the columns and separated. The resulting fractions were named Col31 to Col36.

The CNT solution that did not bind to any of the columns in the end was collected as metallic CNTs (Metal).

Photoabsorption Spectral Measurement and Raman measurement

Figure 2B:
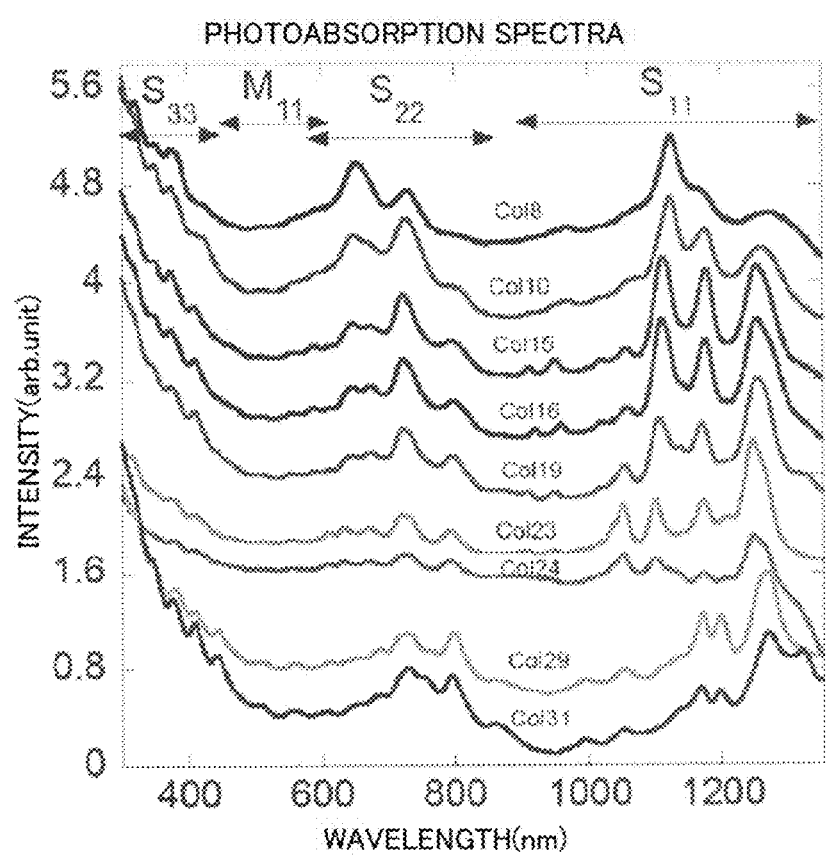
FIG. 2B represents photoabsorption spectra of a separated sample (HiPco-CNT).
Figure 2C:
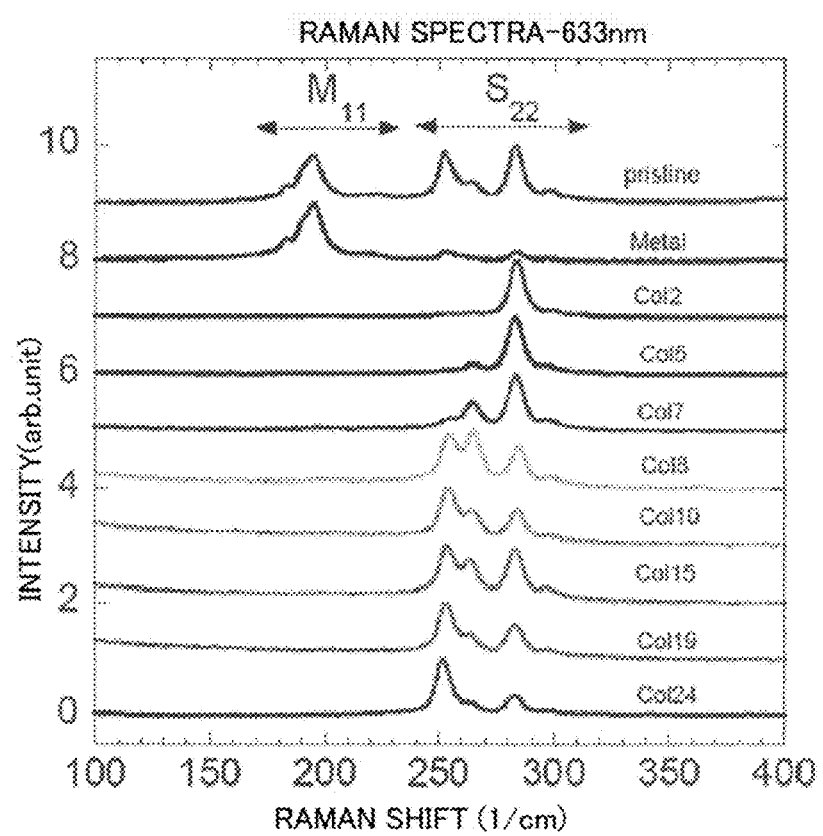
FIG. 2C represents Raman spectra of a separated sample.

FIGS. 2A and 2B represent the photoabsorption spectra of the separated sample. FIG. 2A represents the result before separation (Pristine), and the results for the separated metallic CNTs (Metal), and for the fractions Col1 to Col7 bound to the columns. FIG. 2B represents the results for the selected fractions from Col8 to Col31. The result that each fraction had a different peak shape shows that the semiconducting CNTs were structurally separated. By taking $S_{11}$ or $S_{22}$ as an example, the absorption peak had the tendency to shift toward the longer wavelength side with increasing fraction numbers. In other words, there was a tendency for CNTs of smaller diameters to bind to the columns sooner than CNTs having larger diameters.

FIG. 2C represents the results of the Raman spectral measurements of the separated sample. The results of Raman measurements also showed that CNTs of smaller diameters had the tendency to bind to the columns sooner, and the results coincided with the results obtained from the photoabsorption spectra.

Figure 3:
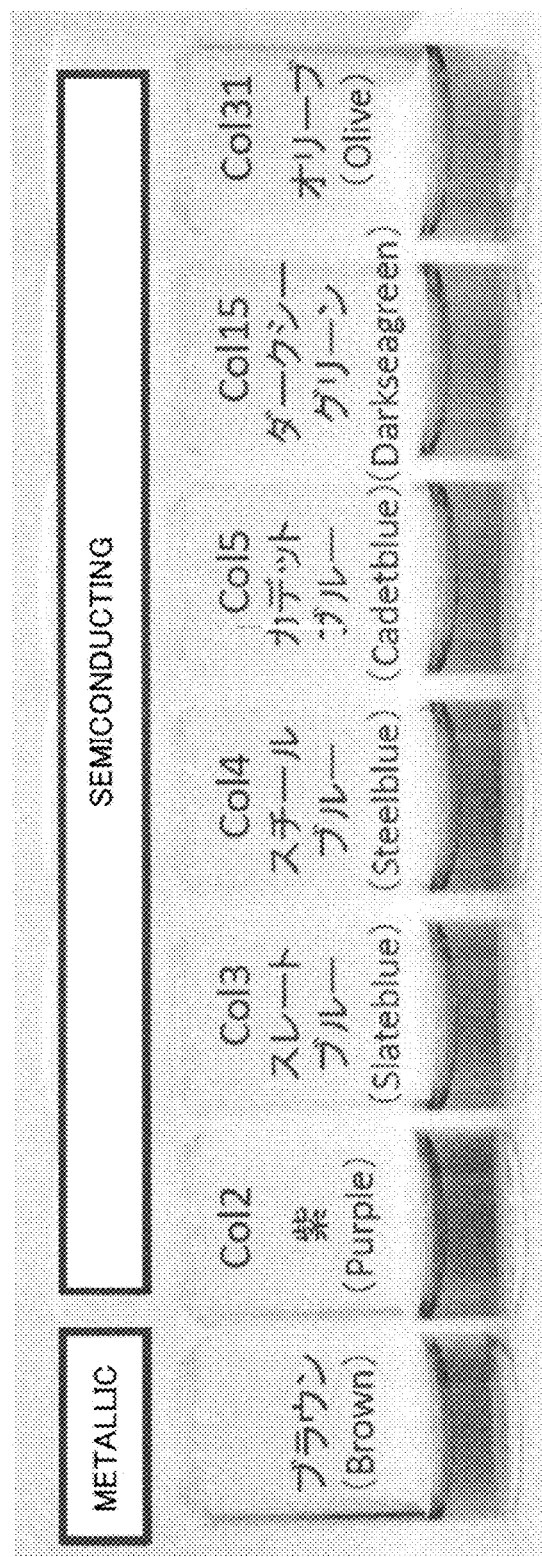
FIG. 3 shows a photograph of a separated sample.

Shifting in the photoabsorption spectra means that the color of the separated CNT solution is different in each fraction. FIG. 3 shows a picture of the solutions of the separated fractions, with the metallic fraction showing a brown color, and the semiconducting fractions showing bright color changes from purple to green.

Fluorescence Spectral Measurement

Figure 4B:
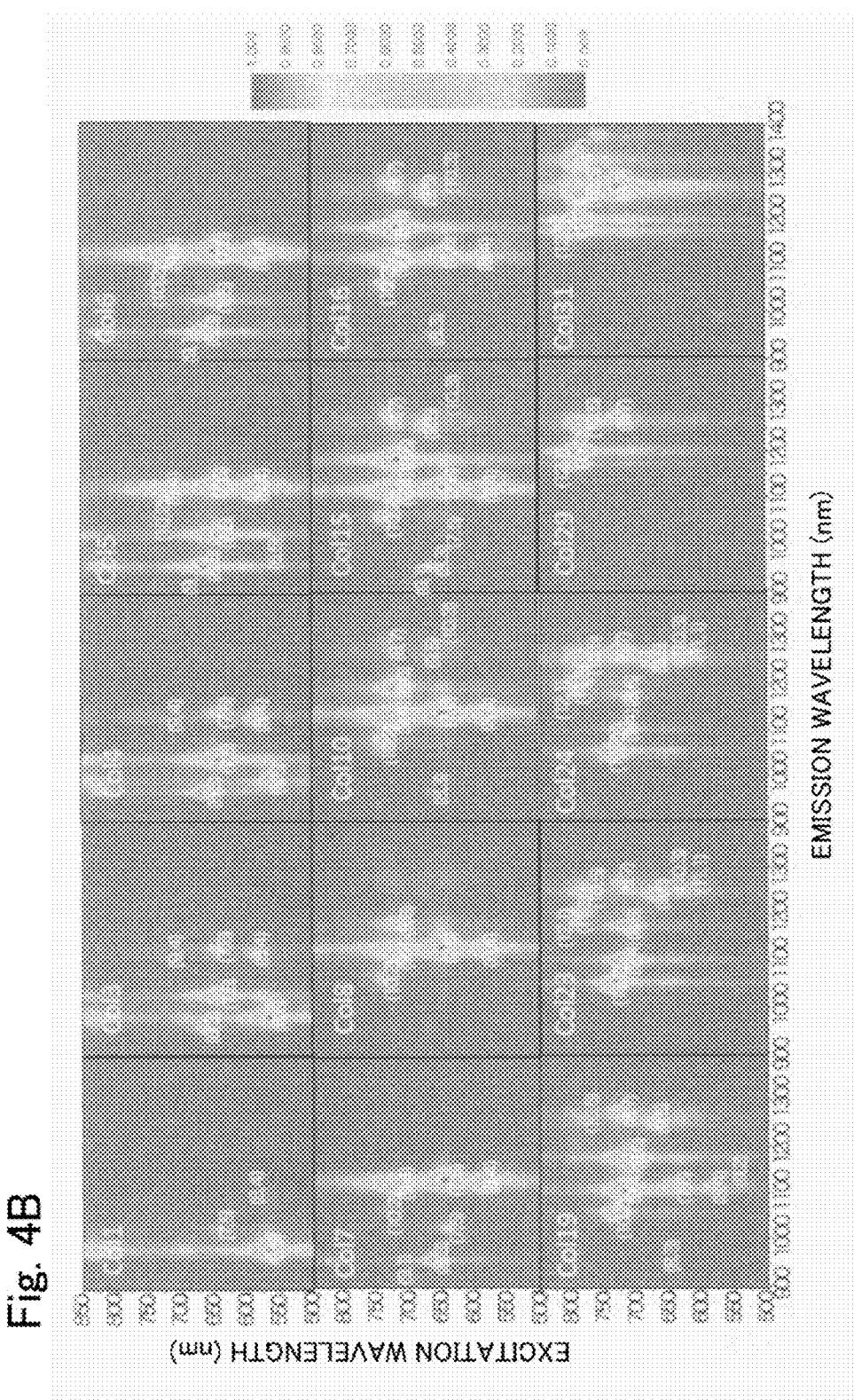
FIG. 4B represents the result of fluorescence spectral measurement (HiPco-CNT; fractions after separation). The fluorescence intensity is represented by a contour plot of fluorescence wavelength (horizontal axis) against excitation wavelength (vertical axis). The figure indicates that the intensity increases in color density order of brighter spots to darker spots over the dark background (see the scale on the right of the figure). Main spots are appended with chiral indices.

As described above, fluorescence spectral measurement enables the individual detection of single-structure semiconducting CNTs, and provides more detailed information. FIG. 4B represents the results for the selected fractions (from Col1 to Col31) eluted from each column. The CNTs were separated to substantially single (6,5) CNTs in Col1, and similarly CNTs of specific chiralities were concentrated in Col4 (7,5), Col8 (7,6), Col16 (8,6), Col24 (10,2), and Col29 (11,3). The proportion of the (6,5) CNTs in the Col1 fraction was calculated to be about 80% of the peak intensity.

These results show that more than one kind of single-chirality CNTs can be simultaneously separated and collected by addition of excess amounts of CNTs by using columns connected in series.

Example 3

Figure 5:
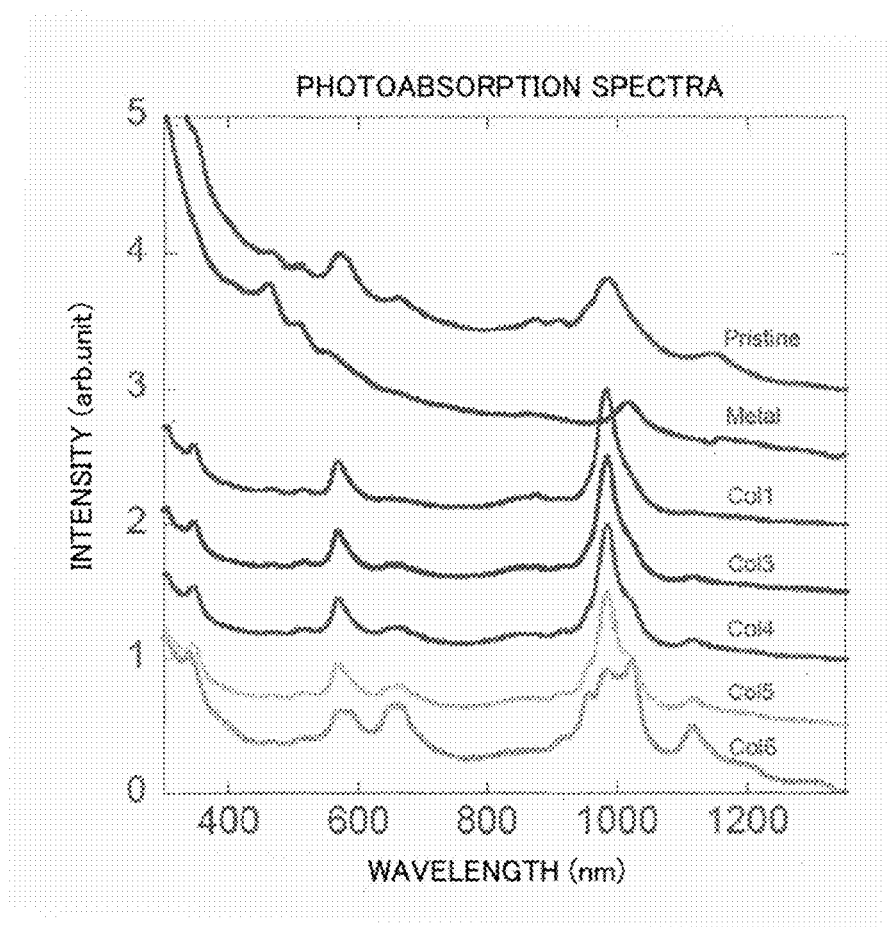
FIG. 5 represents photoabsorption spectra of a separated sample (CoMoCAT-CNT).
Figure 6A:
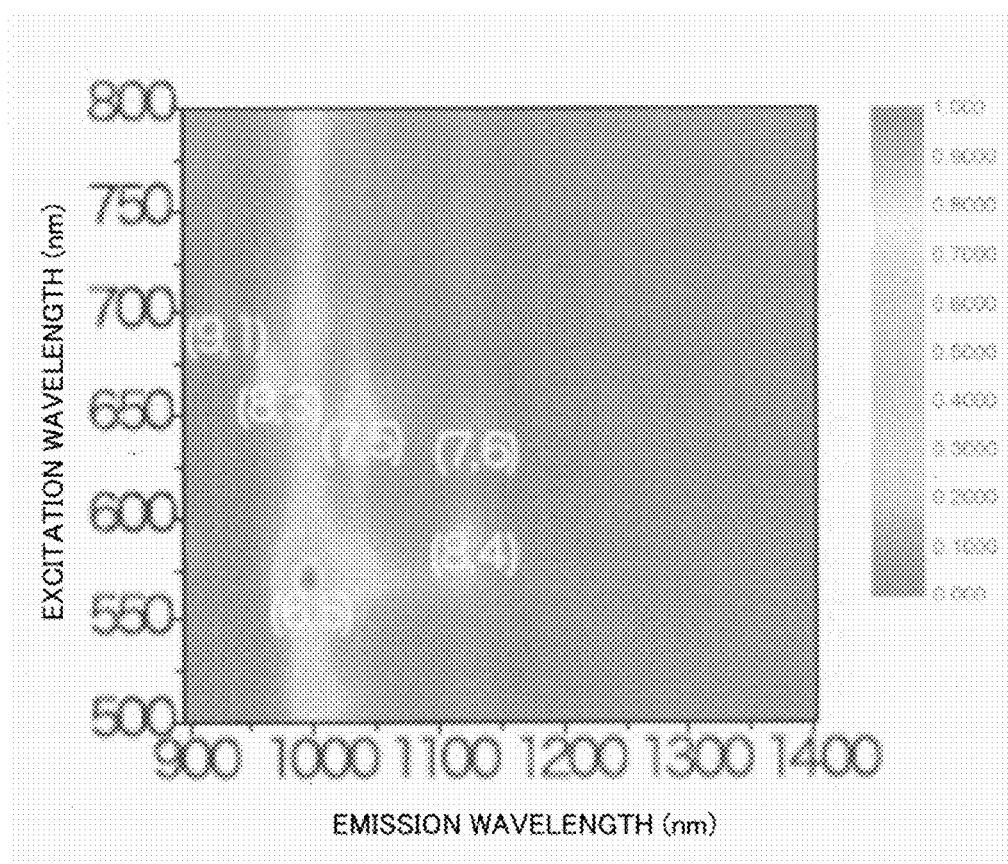
FIG. 6A represents the result of fluorescence spectral measurement (unseparated sample; CoMoCAT-CNT).
Figure 6B:
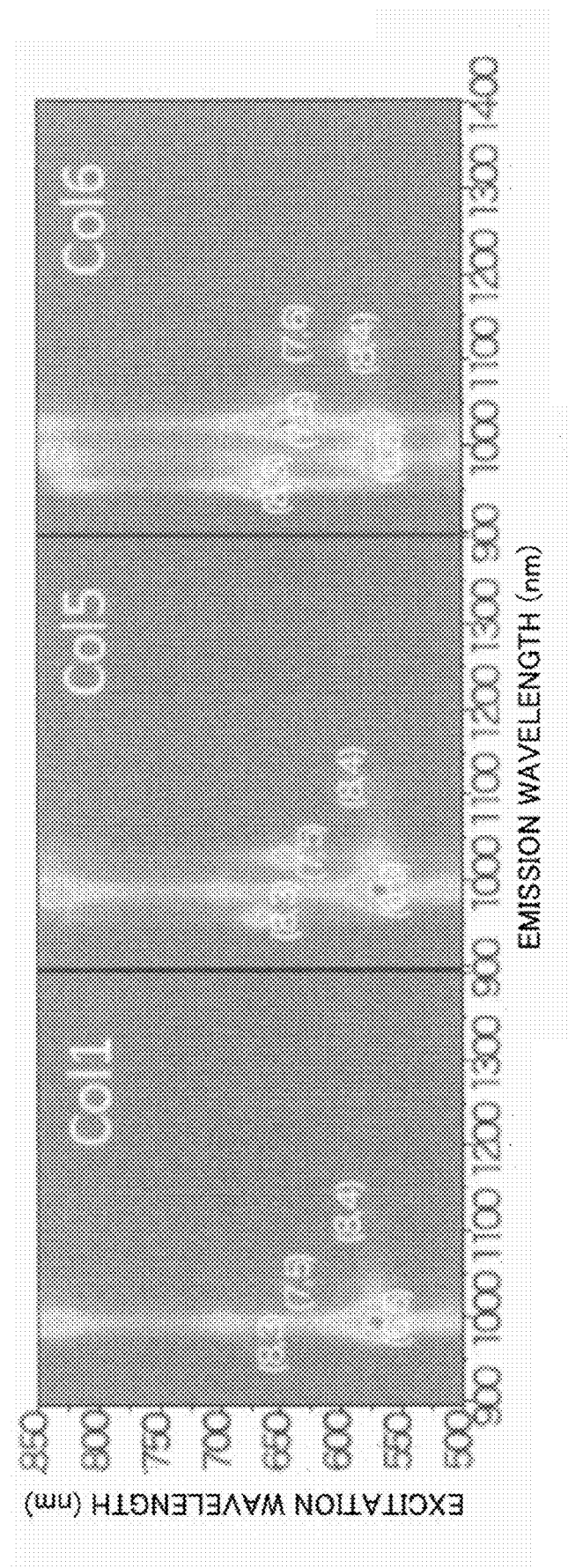
FIG. 6B represents the result of fluorescence spectral measurement (separated sample; CoMoCAT-CNT).
Figure 7:
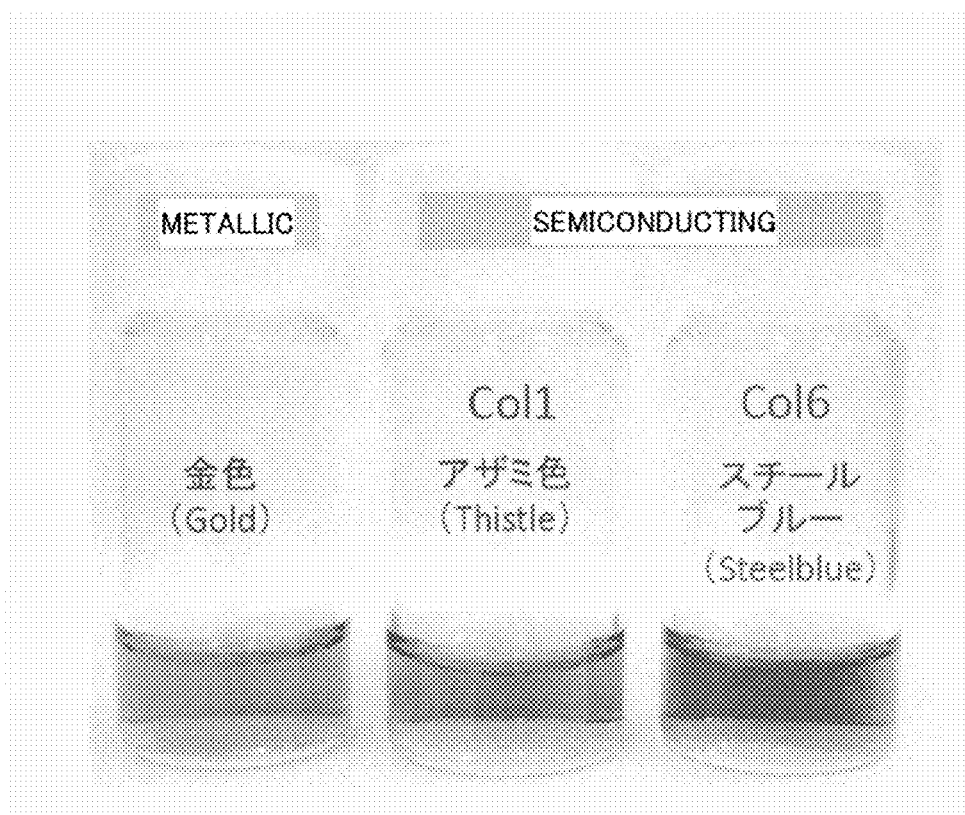
FIG. 7 shows a photograph of a separated sample (CoMoCAT-CNT).

The same experiment conducted in Example 2 was performed by using different CNTs (CoMoCAT-CNTs, Southwest Nano Technologies; diameter 0.8±0.1 nm). Six columns charged with Sephacryl S-300 were connected in series, and a 10-ml CNT dispersion was added thereto. Two cycles of separation using a 2% SDS aqueous solution as a developing solvent were repeated, and the CNT solution that did not bind to any of the columns was collected as metallic CNTs (Metal). Almost all of the semiconducting CNTs adsorbed with a 2% SDS solution, because the CNTs used in this experiment had small diameters, and were strongly adsorbable by the gel. Accordingly, the third adsorption experiment using a lowered SDS concentration was not conducted. The results of photoabsorption spectral measurement using the CoMoCAT-CNT showed the tendency for CNTs of smaller diameters to adsorb on the columns sooner than the thicker CNTs (FIG. 5). FIG. 6 represents the result of fluorescence spectral measurement. The CoMoCAT-CNT sample inherently contains a large proportion of (6,5) CNTs (FIG. 6A, unseparated sample). The proportion of the (6,5) CNT in the Col1 fraction after the separation reached about 85% of the peak intensity, and CNTs of higher singularity were obtained compared with the HiPco-CNT sample. The solution color was gold in the metallic CNTs, and thistle and steel blue in Col1 and Col6, respectively (FIG. 7).

Figure 8A:
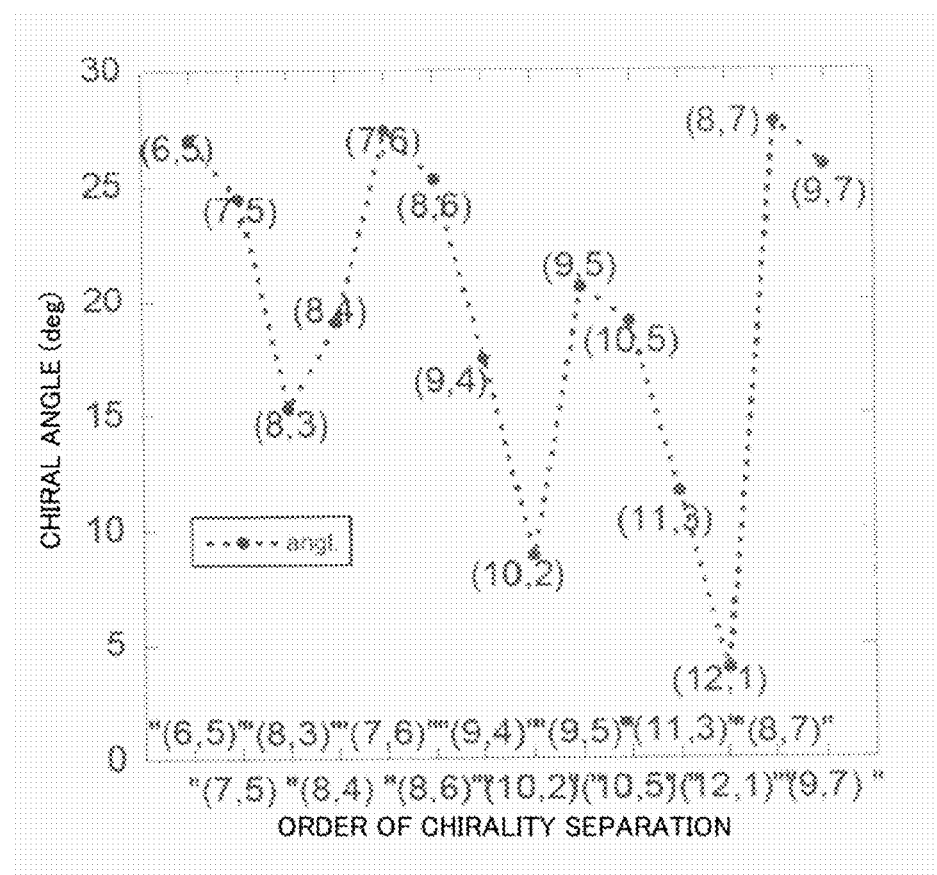
FIG. 8A represents the chirality order of the CNTs separated with series columns plotted against chiral angle.
Figure 8B:
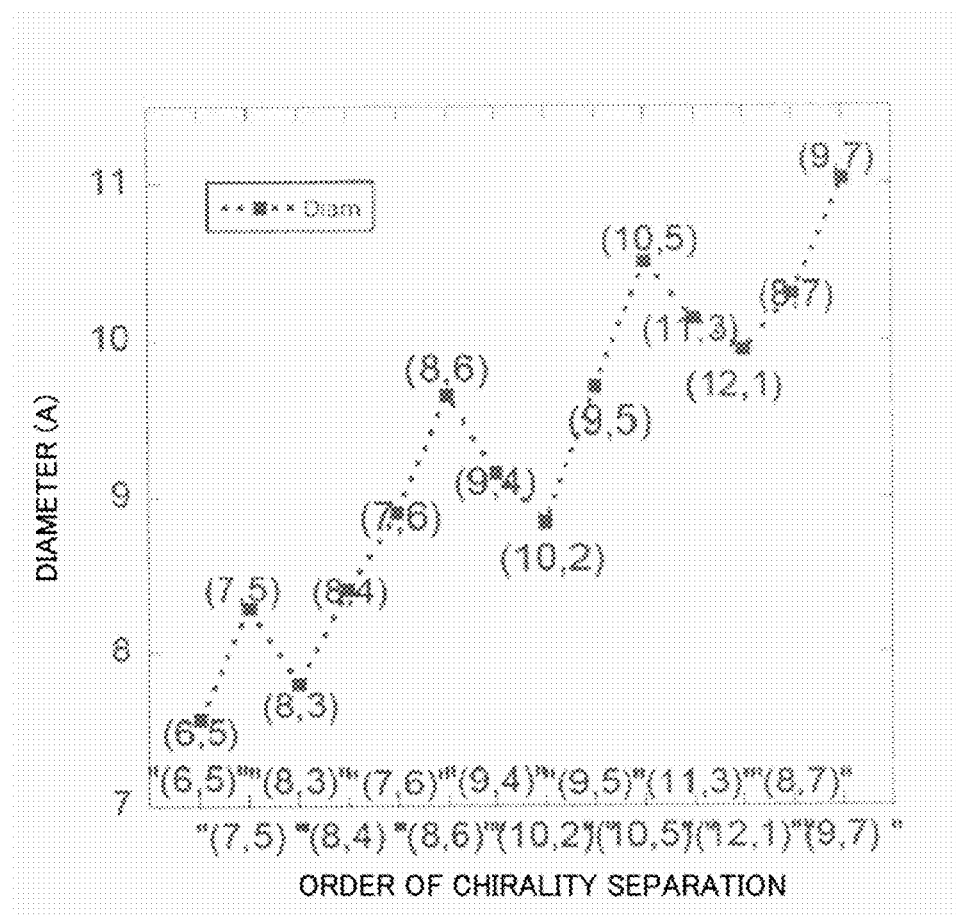
FIG. 8B represents the chirality order of the CNTs separated with series columns plotted against diameter.

Changes in the relative amount of the CNTs of each chirality can be found by comparing the relative fluorescence intensity ratios of the fractions from the results of the fluorescence spectral measurements of Examples 2 and 3. The chirality order of column binding was found to be (6,5), (7,5), (8,3), . . . , (8,7), (9,7), as represented on the horizontal axis of the graph shown in FIG. 8. Plots were drawn using various parameters to find the underlying patterns in the binding order. A plot for chiral angle did not find any such patterns (FIG. 8A). In a plot for diameter, CNTs of smaller diameters bound to the columns and were separated before the other CNTs, though there were some exceptions (FIG. 8B). This result coincides with the results of the photoabsorption spectral measurement and the Raman measurement. FIG. 8C represents the result of plotting the order of separation against the local curvature radius that represents the extent of the bond curvature between the carbon atoms in cylindrical CNTs (Non-Patent Document 9: J. Phys. Chem. C 111, (2007) 9671-9677). It was found that CNTs with smaller local curvature radii more strongly bound to the gel than CNTs having greater local curvature radii, and that the CNTs with greater local curvature radii were separated by binding to the later columns. The variation was less, and the correlation was stronger than in the result of the plot for diameter (FIG. 8B).

Because of the graphene cylindrical structure, CNTs have an electron structure similar to that of graphene. As with graphene, CNTs have electrons involved in binding, and π electrons not involved in binding. It is the property of this n electron that determines the CNT property. The π electrons have electron orbitals vertical to the hexagonal grid. In CNTs, because of the round graphene sheet having a curvature, the inner π orbital of the CNTs has a large overlap with the adjacent 7 electron orbital, whereas the overlap is small in the CNT outer π electron orbitals. Thus, the t electrons orbit to avoid the orbital overlap, and as a result the orbital center shifts, and the orbital extends toward the outer side of the CNTs. Here, such an outward extension of the π electron orbital is greater in CNTs having a large $sp^2$ bond curvature (deviation from the original plane of the $sp^2$ hybrid orbital; specifically, CNTs with smaller local curvature radii). CNTs with greater outward extensions of the 7 electron orbital involve greater interaction between the π electrons and the Sephacryl molecules, and thus provide a strong bond with the gel. This is believed to be the basis of the structural separation of the CNTs in order of bond curvature radius size, as represented in FIG. 8C.

The invention claimed is:

1. A method for separating and collecting a carbon nanotube, comprising:
   a step of adsorbing a carbon nanotube having strong gel adsorbability to a gel by adding a carbon nanotube dispersion containing a carbon nanotube to the gel, then
   a step of separating a solution containing an unadsorbed carbon nanotube having weak gel adsorbability from the gel by adding a solution to the gel, and then
   a step of removing the carbon nanotube adsorbed to the gel by adding an elution solution differing from the solution to the gel after the separation step,
   wherein the carbon nanotube dispersion containing the carbon nanotube is added in excess of a carbon nanotube amount adsorbable by the gel.

2. A method for separating and collecting a carbon nanotube, comprising:
   a step of adsorbing a carbon nanotube having a first to an nth strongest gel adsorbability to a gel charged in each column in is stages of columns connected in series (n≥2, where is a natural number) by adding a carbon nanotube dispersion containing a carbon nanotube to the column of the first stage until the carbon nanotube adsorbs to the gel in the column of the nth stage, then
   a step of separating a solution containing a weakly adsorbable carbon nanotube adsorbed by none of the gels in the columns from the gels in the columns by adding a solution to the gels in the columns, and then
   a step of removing n different carbon nanotubes having different levels of adsorbability and adsorbed to the gels in each respective column by adding an elution solution differing from the solution to the gels in each colunm individually,
   wherein the carbon nanotube dispersion containing the carbon nanotube is added in excess of a carbon nanotube amount adsorbable by the gel.

3. The method according to claim 1 or 2, wherein a strongly adsorbable semiconducting carbon nanotube of a specific structure is removed from the gel after the separation.

4. The method according to claim 3, wherein a semiconducting carbon nanotube having a specific diameter as the specific structure is removed from the gel after the separation.

5. The method according to claim 3, wherein a semiconducting carbon nanotube having specific chirality as the specific structure is removed from the gel after the separation.

6. The method according to claim 3, wherein a semiconducting carbon nanotube having a specific local curvature radius as the specific structure is removed from the gel after the separation.

7. The method according to claim 1, wherein the gel is charged in a column.

* * * * *